United States Patent [19]

Malacrida et al.

[11] Patent Number: 4,921,957
[45] Date of Patent: May 1, 1990

[54] NOVEL FLUORINATED COMPOUNDS AND PROCESS FOR PREPARING THEM

[75] Inventors: Alessandro Malacrida, Sovico, Italy; Darryl D. Desmarteau, Clemson, S.C.

[73] Assignee: Ausimont S.r.l., Milan, Italy

[21] Appl. No.: 375,948

[22] Filed: Jul. 6, 1989

[30] Foreign Application Priority Data

Jul. 7, 1988 [IT] Italy ............................. 21266 A/88

[51] Int. Cl.$^5$ ................. C07D 251/00; C07D 271/06; C07D 271/12
[52] U.S. Cl. ..................................... 544/217; 548/131; 564/510; 564/487
[58] Field of Search ......................... 548/131; 544/217; 564/510

[56] References Cited

PUBLICATIONS

Banks et al., Chem. Abstracts; 95, 7; 61366g (1981).

*Primary Examiner*—Mary C. Lee
*Assistant Examiner*—J. Richter
*Attorney, Agent, or Firm*—Stevens, Davis, Miller & Mosher

[57] ABSTRACT

By reacting 3,3,4,4-tetrafluoro-2-(trifluoromethyl)-1,2-oxazetidine (I) with a Lewis acid, in particular SbF$_5$, three novel fluorinated compounds (II), (III) and (IV) are obtained:

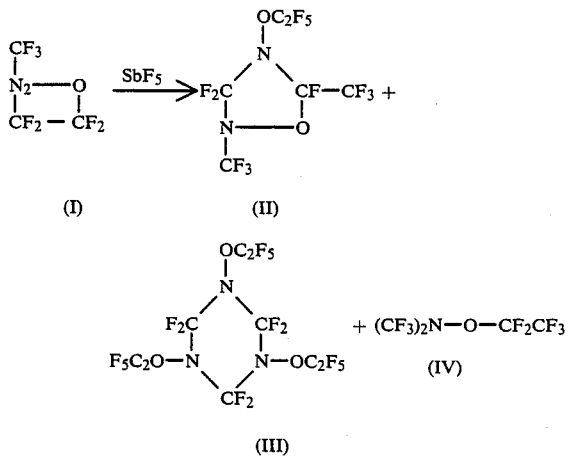

The compounds are useful as lubricants.

3 Claims, No Drawings

NOVEL FLUORINATED COMPOUNDS AND PROCESS FOR PREPARING THEM

DESCRIPTION OF THE INVENTION

The present invention relates to novel fluorinated compounds, and to a process for preparing them.

More particularly, it relates to three novel fluorinated compounds obtained by reacting 3,3,4,4,-tetrafluoro-2-(trifluoromethyl)-1,2-oxazetidine:

(I)

with a Lewis acid.

The above said oxazetidine of formula (I) is a known compound, described by D. A. Barr et al. in J. Chem. Soc. 1955, 1881.

It has now been discovered, according to the present invention, that such compound reacts with a Lewis acid generating three novel fluorinated compounds.

An object of the present invention is to provide the said novel fluorinated compounds.

Another object is to provide a process for preparing them.

The first object is achieved by providing the following three novel compounds:

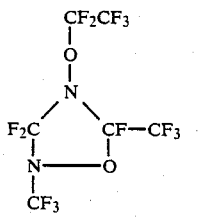

(II)

3,3,5-trifluoro-2,5-di(trifluoromethyl)-4-(1,1,2,2,2-pentafluoroethoxy)-1,2,4-oxadiazolidine;

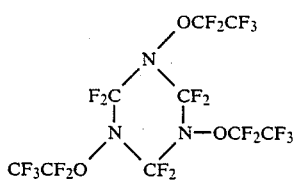

(III)

2,2,4,4,6,6-hexafluoro-1,3,5-tris(1,1,2,2,2-pentafluoroethoxy)-1,3,5-triazine;

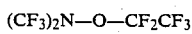 (IV)

N,N-bis(trifluoromethyl)-N-(1,1,2,2,2-pentafluoroethoxy)-amine.

The compound (II) which is a liquid with a boiling temperature of 75° C., is useful as a lubricant, as a heat transfer medium, and as a test fluid for electronic components.

The compound (III), a solid compound with a melting point of 60°-61° C., is useful as a lubricant.

The compound (IV), a low-boiling liquid, with a boiling temperature of 27° C., is useful as a test fluid for electronic components, and as a heat transfer medium.

These three compounds are prepared simultaneously by the process according to the present invention. This process is characterized in that 3,3,4,4-tetrafluoro-2-(trifluoromethyl)-1,2-oxazetidine (I) is reacted with a Lewis acid.

The reaction is usually carried out at a temperature within the range of from 0° to 100° C., and preferably from 10° to 40° C.

As the Lewis acid, $SbF_5$ is preferably used.

The molar ratio of the Lewis acid, computed as $SbF_5$, to the oxazetidine (I) is usually with the range of from 0.1 to 2.0, and preferably from 0.9 to 1.1.

The reaction may be carried out batchwise, inside an autoclave, under the autogenous pressure of the system. The reaction time is generally within the range of from 1 minute to 24 hours.

At the end of the reaction, the reaction mixture is treated with a neutralizing agent in order to neutralize $SbF_5$.

As the neutralizing agent, is particular NaF is used. The molar ratio of such an agent, computed as NaF, to $SbF_5$, is usually within the range of from 1 to 50; and preferably from 5 to 15.

The following example is given for the purpose of still better illustrating the invention but without limiting it.

EXAMPLE

Inside a Teflon tubular reactor having a volume of 20 ml provided with a valve, the following compounds are condensed in the same order as shown, at the temperature of liquid nitrogen ($-196°$ C.):

2.88 g (13.3 mmol) of $SbF_5$; and 2.90 g (14.6 mmol) of oxazetidine (I).

The oxazetidine was prepared by reacting

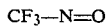

with $CF_2=CF_2$ (D. A. Barr et al., J. Chem. Soc. 1955, 1881).

The thus-charged reactor is maintained at 20° C. for 12 hours.

To the raw reaction mixture, cooled down to $-196°$ C. and under an anhydrous nitrogen atmosphere, 5.60 g (133 mmol) of fine NaF powder is added.

The thus-charged reactor is maintained at 20° C. for a further 24 hours and, in order to achieve a good solid-liquid contact, is repeatedly shaken.

The reaction products are recovered by being transferred, under a low pressure ($10^{-3}$ torr), from the reactor into a cold trap maintained at a temperature of $-196°$ C.

This step requires 24 hours.

The mixture of the reaction products is distilled under a pressure of $10^{-3}$ torr.

The vapors coming from the distillation kettle are made to flow through cold traps maintained at temperatures of $-50°$ C., $-85°$ C., $-110°$ C., and $-196°$ C.

Inside the trap at $-50°$ C., 145 mg of compound (III) is collected, with a molar yield of 5% relative to oxazetidine (I).

The compound (III) was characterized as follows:

Mass spectrum: chemical ionization (CI), CI gas=$CH_4$, m/z 598 (MH+) 578 (MH-HF+).

Infrared spectrum: main absorption bands (cm$^{-1}$): 1391 (d), 1332 (d), 1289 (F), 1242 (f), 1180 (m), 1089 (f), 946 (m).

$^{19}$F-N.M.R. spectrum: (internal reference: CFCl$_3$; solvent: CDCl$_3$; temperature = 50° C.).

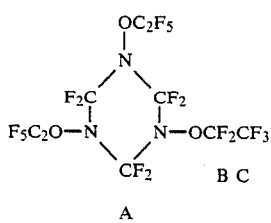

A = 84.7 ppm
B = 93.0 ppm
C = 84.7 ppm

NOTE: These represent chemical shifts of F atoms in the relative groups with reference to the internal compound CFCl$_3$.

Inside the trap at −85° C., 1.37 of compound (II) is collected, with a molar yield of 47% relative to oxazetidine (I).

The compound (II) was characterized as follows:

Mass spectrum: chemical ionization (CI), CI gas = CH$_4$, m/z, 399 (MH+), 379 (MH-HF+).

Infrared spectrum: main absorption bands (cm$^{-1}$): 1362 (d), 1315 (m), 1282 (m), 1246 (f), 1225 (f), 1179 (m), 1120 (m), 1098 (f), 942 (d).

$^{19}$F-N.M.R. spectrum: (internal reference: CFCl$_3$; solvent: CDCl$_3$).

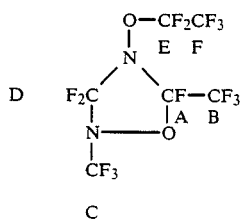

A = −111.6 ppm
B = −82.3 ppm
C = −66.7 ppm
D = −78.7 ppm; −83.1 ppm (AB system)
E = −90.1 ppm; −95.2 ppm (AB system)
F = −84.7 ppm NOTE: These represent chemical shifts of F atoms in the relative groups with reference to the internal compound CFCl$_3$.

Inside the trap at −110° C., 0.42 g of compound (IV) is collected, with a molar yield of 10% relative to oxazetidine (I).

The compound (IV) was characterized as follows:

Mass spectrum: chemical ionization (CI), CI gas = CH$_4$, m/z, 288 (MH+), 287 (M+), 258 (M-F).

Infrared spectrum: main absorption bands (cm$^{-1}$): 1361 (d), 1319 (f), 1272 (f), 1240 (f), 1218 (f), 1183 (f), 1095 (f), 1035 (d), 970 (m), 713 (m).

$^{19}$F-N.M.R. spectrum: (internal reference: CFCl$_3$; solvent: CDCl$_3$).

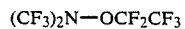

A = −67.9 ppm
B = −94.3 ppm
C = −85.0 ppm

NOTE: These represent chemical shifts of F atoms in the relative groups with reference to the internal compound CFCl$_3$.

Inside the trap at −196° C., 0.25 g of oxazetidine (I) is collected.

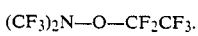

What is claimed is:

1. 3,3,5-trifluoro-2,5-di(trifluoromethyl)-4-(1,1,2,2,2-penta-fluoroethoxy)-1,2,4-oxadiazolidine:

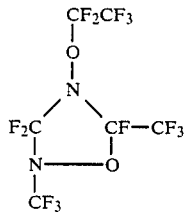

2. 2,2,4,4,6,6-hexafluoro-1,3,5-tris(1,1,2,2,2-penta-fluoroethoxy)-1,3,5-triazine:

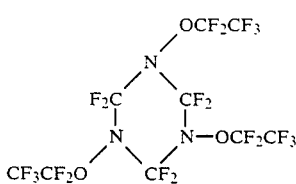

3. N,N-bis(trifluoromethyl)-N-(1,1,2,2,2-pentafluoroethoxy)-amine: